United States Patent [19]
Hama et al.

[11] Patent Number: 5,179,943
[45] Date of Patent: Jan. 19, 1993

[54] MEDICAL APPARATUS USING OZONE GAS

[75] Inventors: Mamoru Hama, Chino; Matao Mitsuyoshi, Chiyoda; Takahiro Hashimoto, Shimabara, all of Japan

[73] Assignees: Kabushiki Kaisha Mihama Seisakusho, Nagano; Yugen Kaisha Aoi Shoji, Nagasaki, both of Japan

[21] Appl. No.: 690,919

[22] PCT Filed: Oct. 24, 1990

[86] PCT No.: PCT/JP90/01369

§ 371 Date: Jun. 13, 1991

§ 102(e) Date: Jun. 13, 1991

[87] PCT Pub. No.: WO91/06275

PCT Pub. Date: May 16, 1991

[30] Foreign Application Priority Data

Oct. 25, 1989 [JP] Japan .................... 1-277942
Oct. 25, 1989 [JP] Japan .................... 1-277943

[51] Int. Cl.$^5$ ............................................ A61H 33/00
[52] U.S. Cl. ............................ 128/368; 128/202.25; 128/367
[58] Field of Search ............... 128/200.14, 200.15, 128/375, 370, 202.25, 66, 200.21, 366, 367, 368; 4/535

[56] References Cited

U.S. PATENT DOCUMENTS

| 951,789 | 3/1910 | Ashley | 128/202.25 |
| 3,815,595 | 6/1974 | Bar | 128/200.14 |
| 4,691,695 | 9/1987 | Birk et al. | 128/375 |

FOREIGN PATENT DOCUMENTS

| 3214335 | 10/1983 | Fed. Rep. of Germany | 128/66 |
| 2403085 | 5/1979 | France | 128/202.25 |
| 62-144659 | 6/1987 | Japan | |
| 2-019156 | 1/1990 | Japan | 4/535 |
| 980729 | 12/1982 | U.S.S.R. | 128/202.25 |

Primary Examiner—Mark Graham
Attorney, Agent, or Firm—Jordan and Hamburg

[57] ABSTRACT

Medical apparatus of the present invention effectively uses ozone as an anesthetic by spraying ozone gas onto affected bodily parts such as hands, arms, legs. Upon inserting affected parts in an airtight body, ozone gas is circulated in the airtight body; likewise, a sprayer for spraying ozone gas onto affected bodily parts is provided in a hood, which is attached to a conduit member having a feeding path and a withdrawing path, so as to feed ozone gas to the inner space of the hood.

8 Claims, 2 Drawing Sheets

5,179,943

MEDICAL APPARATUS USING OZONE GAS

FIELD OF TECHNOLOGY

The present invention relates to a medical apparatus using ozone gas, and more precisely relates to a medical apparatus spraying ozone gas to affected bodily parts to anesthesize them.

BACKGROUND TECHNOLOGY

Ozone is a quite strong oxidizing agent and its use for sterilization, decoloration, deodorization, etc. has been known. Conventionally, ozone gas has been used for various procedures.

For example, its sterilization ability is used for purifying rooms, sterilizing food for storage, sterilizing water in water supply systems and pools, and disinfecting wounds and facia; its decoloration and deodorization abilities are used for deodorizing water supply systems and sewage disposal systems, and purifying air in hotels and hospitals; furthermore, ozone is used for oxidization, ozonoloysis, surface activation, etc.

As described above, ozone gas is generally used industrially for sterilization, decoloration and deodorization. Furthermore, considering its sterilization ability, there have been some proposals to use ozone for sterilizing wounds, for curing athlete's foot and for facial culture for stimulating skin and accelerating blood circulation.

The inventors studies usages of ozone gas and found that ozone gas has not only the above described functions but also a pronounced anesthetic effect. For example, it has been found that a pain caused by inflammation of a sprain can be effectively reduced by spraying ozone gas onto the affected part. This anesthetic effect cna be attained simply by spraying ozone gas onto affected bodily parts, and it is found that ozone gas is capable of reducing pains in various bodily parts, such as lumbar region, joints, etc.

The anesthetic function is different from above described sterilization, decoloration and deodorization, and the anesthetic function will be effective in the medical field. The present invention is directed to the pain-killing function of ozone gas, and an object of the invention is to provide a medical apparatus using ozone gas, which is capable of easily anesthesizing affected bodily parts, such as arms, legs, etc.

DISCLOSURE OF THE INVENTION

The medical apparatus of the present invention comprises:

an airtight body for hermetically accommodating affected bodily parts such as hands, arms, legs, the airtight body having an opening through which the affected bodily parts can be inserted therein;

a gas feeding mechanism connected to an ozonizer, the feeding mechanism communicating with the airtight body so as to feed ozone gas thereto; and a gas discharge mechanism for discharging ozone gas from the airtight body while maintaining the internal pressure thereof. In this apparatus, ozone gas is introduced into the airtight body, so that the epidermis about affected bodily parts is uniformly exposed to ozone gas. Thus, ozone gas will effectively reduce pains in affected bodily parts.

Furthermore, the medical apparatus may comprise:

an ozonizer having a gas feeding mechanism, which forms and feeds ozone gas, and a gas withdrawing mechanism;

a conduit member having a gas path and a gas withdrawing path, one end of the tubing member communicating with the gas feeding mechanism and the gas withdrawing mechanism, the feeding path communicating with the gas feeding mechanism and the withdrawing path communicating with the gas withdrawing mechanism;

a hood provided at the other end of the tubing member; and a sprayer of generally cylindrical shape, the sprayer being provided in the hood, and having through-holes through which ozone gas passes. In this apparatus, by enclosing affected bodily parts within the hood, the affected bodily parts can be effectively and uniformly exposed to ozone gas.

BRIEF DESCRIPTION OF THE DRAWINGS

Embodiments of the invention will now be described by way of example and with reference to the accompanying drawings, in which.

DETAILED DESCRIPTION OF PREFERRED EMBODIMENTS

Preferred embodiments of the present invention will now be described in detail with reference to accompanying drawings.

A first embodiment of the medical apparatus using ozone gas will be explained with reference to FIGS. 1 and 2.

Figure 1:
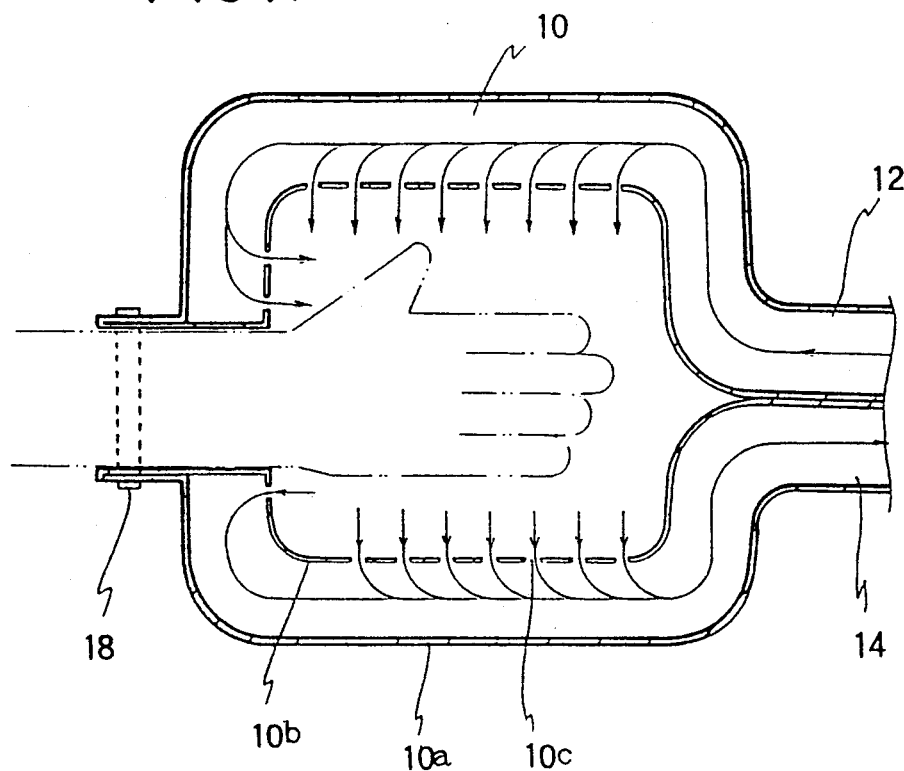
FIG. 1 is an explanatory view showing a main part of a first embodiment and its state of usage.

In the apparatus of this embodiment, an affected bodily part is inserted in an airtight body 10 via an opening as shown in FIG. 1, so as to hermetically accommodate the affected bodily part therein, and ozone gas is sprayed into the airtight body 10 and is withdrawn therefrom.

Figure 2:
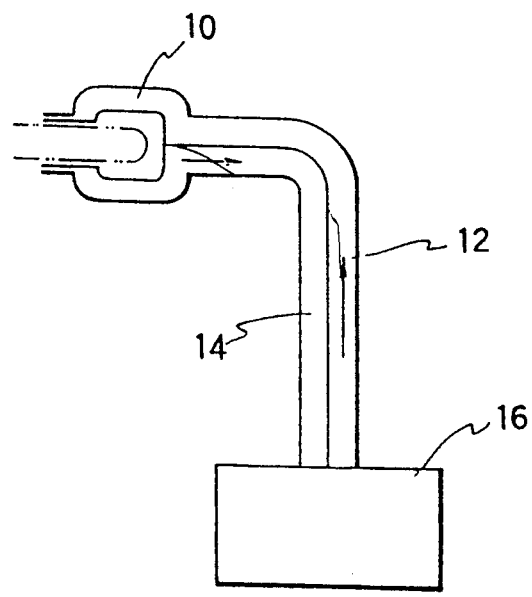
FIG. 2 is an explanatory view showing a whole structure of the first embodiment.

The airtight body 10, as shown in FIG. 2, communicates with an ozonizer 16 via a spraying path 12 and withdrawing path 14. The spraying path 12 and the withdrawing path 14 are made of plastics having resistance to degradation by ozone. The ozonizer has a known structure, e.g. a discharge tube, etc., and further has a gas feeding mechanism for feeding a prescribed quantity of ozone gas and a gas withdrawing mechanism.

FIG. 1 shows an example of treating a hand, the airtight body 10 being provided at one end with an opening through which the hand or other affected bodily part is inserted into the airtight body 10; the spraying path 12 and the withdrawing path 14 extend to the other end of the airtight body 10. The airtight body 10 is made of plastic film in the form of a soft and elastic bag. The hand is hermetically accommodated in the airtight body 10 by binding a band 18 around the arm after inserting the hand therein. In case of arms, legs, etc, as affected bodily parts, they may be similarly inserted therein and bound by the band 18.

The airtight body 10 consists of an outer bag 10a and an inner bag 10b which are ozone resistant. The airtight body 10 is divided into an upper half section and a lower half section, the upper half section communicating with the spraying path 12 and the lower half section communicating with the withdrawing path 14. There are bored through holes 10c for passing ozone gas into and out of the inner bag 10b. Note that, the affected bodily part is preferably spaced from the inner face of the inner bag 10b when the affected bodily part is inserted in the airtight body 10.

Usage of the above described apparatus will be explained hereinafter.

The affected part is inserted in the airtight body 10 through the opening and the band 18 is bound around the opening to hermetically seal the airtight body 10. Then, the ozonizer 16 forms and feeds ozone gas via the spraying path 12. Ozone gas is introduced into the space between the outer bay 10a and the inner bag 10b and goes into the inner space of the inner bag 10b via the through-holes 10c, and then ozone gas enters the withdrawing path 14 via the through-holes 10c.

Preferably, ozone gas pressure in the airtight body 10 is maintained during the operation. Namely, the inner bag 10b is expanded so that the affected part is spaced from the inner face thereof and the epidermis about the affected bodily part can be uniformly exposed to ozone gas.

Ozone is apt to be resolved by heat, and its density is controlled by water vapor in the atmosphere. Therefore, it is preferable, for maintaining ozone in an active condition (i.e. unresolved) in the airtight body 10, to continuously supply a fixed quantity of ozone gas therein during operation. By controlling the quantity of ozone gas supplied to the airtight body 10, the gas can be prevented from resolution caused by changes in temperature, relative humidity, etc..

The ozonizer 16 controls the inner pressure of the air-tight body 10 by adjusting the quantity of flow and the density of ozone gas. Note that ozone gas withdrawn from the airtight body 10 may be treated to reduce its moisture to enable reuse, or the gas may be released to the atmosphere after a harmless treatment, such as heating. Furthermore, if the density is quite low, the gas can be released to the atmosphere without treatment. In this case, an exhaust-gas-adjusting valve may be attached so as to adjust gas pressure in the airtight body 10.

In the medical apparatus of this embodiment, the medical treatment can be done in the hermetically sealed space without ozone leakage, so that the treatment can be done without exposing the operator and patient to the odor of ozone, and the density of ozone gas can be relatively high compared to that of ozone used for air purification, sterilization, etc..

Furthermore, the apparatus of this embodiment has a simple structure, it is easy to use, and it can be applied to various affected bodily parts, such as arms, legs, by adjusting the size of the airtight body 10.

In case of treating a lower back (lumbar region) or abdomen an airtight body, which covers the lower half of user's body including the affected bodily part, or partly covers the affected bodily part, can be applied to the apparatus. And a large airtight body, which covers a whole human body except his or her head, also can be applied to the apparatus. In this case, the airtight body may be an airtight box communicating with the feeding path 12 and the withdrawing path 14.

The airtight body described above can be changed in its size and structure, so it is not necessarily a double-bag structure as shown in FIG. 1. The essential structural elements are the gas feeding mechanism and the gas withdrawing mechanism so as to cause flow of ozone gas through the airtight body.

(Second Embodiment)

Next, a second embodiment will be explained with reference to FIGS. 3 and 4.

A conduit member 20 for feeding and withdrawing ozone gas has a feeding path 22 for feeding ozone gas and a withdrawing path 24 for withdrawing and discharging ozone gas. The conduit member 20 at one end is connected to an ozonizer 26, as shown in FIG. 4, and the feeding path 22 communicates with the gas feeding mechanism of the ozonizer 26, the withdrawing path 24 communicating with the gas withdrawing mechanism thereof.

Figure 4:
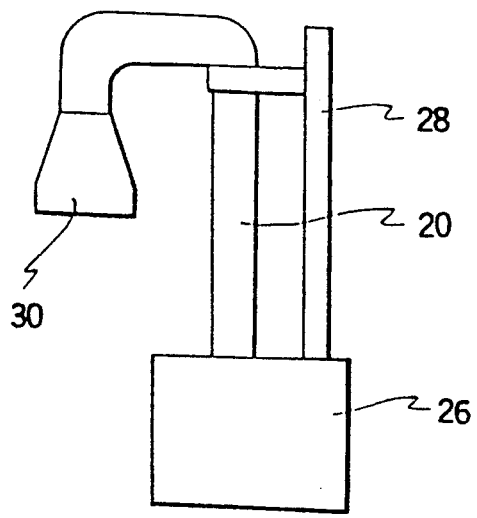
FIG. 4 is an explanatory view showing a whole structure of the second embodiment.

The conduit member 20 is extended upward from the ozonizer 26, and is beat in an L-shape as shown in FIG. 4. At the bent section, the conduit member 20 is supported by a stand 28.

There is fixed a generally cylindrical hood 30, whose diameter is gradually enlarged toward the lower end, at the front end of the conduit member 20. The lower end of the hood 30 faces downward.

Figure 3:
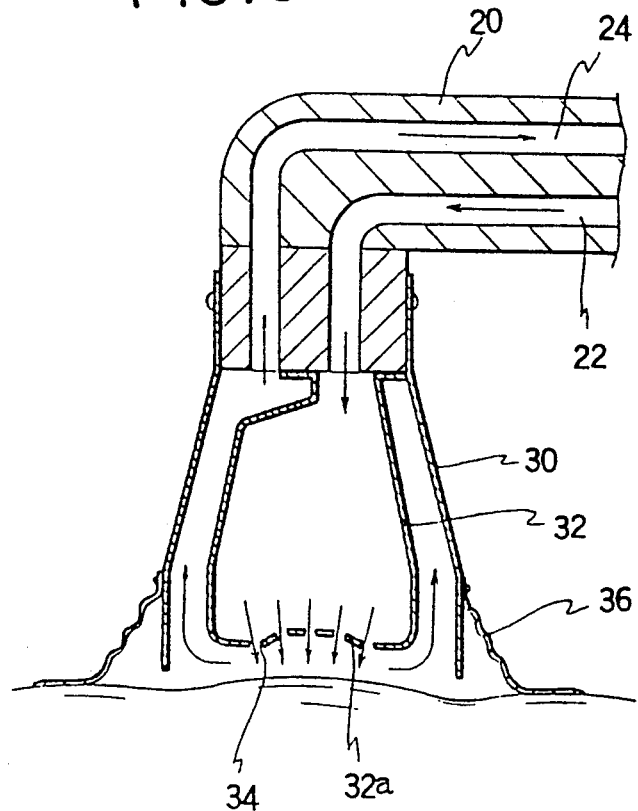
FIG. 3 is an explanatory view showing a main part of a second embodiment and its state of usage.

The front ends of the feeding path 22 and the withdrawing path 24 open into the hood 30, as shown in FIG. 3.

There is fixed a sprayer 32, in the form of a hollow truncated cone, in the hood 30. The sprayer 32 communicates with the forwarding path 22. The sprayer 32 extendes toward the lower end of the hood 30, and the inner diameter thereof is gradually enlarged toward the lower end thereof. There is formed a narrow space between the outer circumferential face of the sprayer 32 and the inner face of the hood 30.

There is formed a spraying section 32a with an end wall in the sprayer 32. The spraying section 32a corresponds to the open lower end of the hood 30. The center of the spraying section 32a is slightly concave, and there are bored through-holes 34 therein so as to pass ozone gas.

Note that the spraying section 32a is located slightly above and substantially parallel to the lower end of the hood 30, so that the lower end of spraying section 32a and the lower end of the hood 30 are not coplanar.

Usage of the above described apparatus will be explained hereinafter.

By positioning affected bodily parts, such as arms, legs, etc., proximate to the open end of the hood 30, ozone gas sprayed from the spraying section 32a contacts the affected bodily parts.

Ozone gas formed by the ozonizer 26 is introduced into the sprayer 32 via the feeding path 22 and sprayed from the through-holes 34. Sprayed ozone gas contact affected bodily parts and returns to the ozonizer 26 via the withdrawing path 24.

Ozone gas sprayed from the sprayer 32 is contained within the hood 30 so as not to leak into the atmosphere, as shown in FIG. 3, and is withdrawn via the withdrawing path 24, so that the gas can be recirculated effectively.

Note that, as shown in FIG. 3, there is provided a skirt 36 around the outer circumferential surface of the lower end of the hood 30. The skirt 36 covers affected parts proximate to the hood 30, so that ozone leakage can be suppressed.

In the apparatus of this embodiment, an affected bodily part can be exposed to ozone gas by positioning the part proximate to the lower end of hood 30, so it is very easy to use the apparatus.

Ozone gas can be easily sprayed onto not only arms and legs but also about the torso. Furthermore, the hood 30 may be provided in a variety of shapes, the conduit member 20 may be flexible, and the conduit member may have a telescopic structure, so that the apparatus can be used more easily and patients can be treated in comfortable positions.

By covering the affected bodily parts by the hood 30 or the skirt 36 to suppress leakage, the quantity of ozone used can be reduced, and relatively high density ozone gas can be used for treatment.

Note that ozone gas is withdrawn in the apparatus but the gas withdrawn can be released to the atmosphere after a harmless treatment, such as heating. On the other hand, the gas withdrawn may be reused. Furthermore, if the density is quite low, the gas can be released to the atmosphere without treatment.

In this embodiment, the sprayer 32 is attached to the feeding path 22. But the paths 22 and 24 may be arranged vice versa and the sprayer 32 may communicate with the path 24. With the latter structure, ozone gas will be sprayed from the hood 30 and be withdrawn via the sprayer 32. In some cases, this alternative structure can further suppress ozone leakage.

Preferred embodiments of the present invention have been described in detail but the present invention is not limited to the above embodiments. Many modifications can be made without deviating from the scope of the invention or the claims.

We claim:

1. A medical apparatus using ozone gas, comprising:
   an airtight body for hermetically accommodating affected bodily parts, said airtight body having an opening through which the affected bodily parts can be inserted therein;
   an ozonizer;
   gas feeding means connected to the ozonizer, said feeding means being in communication with said airtight body so as to feed ozone gas thereto;
   gas withdrawing means for withdrawing ozone gas from said airtight body while maintaining inner pressure thereof;
   and said airtight body comprising an outer bag and an inner bag, the affected parts being insertable into the inner bag, the bags being made of plastic film, a space being formed between the bags as a path for ozone gas, the inner bag having a plurality of through-holes communicating with the path.

2. The medical apparatus according to claim 1, further comprising a band for hermetically sealing affected bodily parts in said airtight body, said band being provided at the opening of said airtight body.

3. The medical apparatus according to claim 1, wherein said gas feeding means comprises means defining a feeding path for ozone gas and said gas withdrawing means comprises means defining a withdrawing path for ozone gas, said airtight body is divided into a first-half section and a second-half section, one of the sections communicating with the feeding path and the other section communicating with the withdrawing path.

4. The medical apparatus according to claim 1, further comprising pressure adjusting means for maintaining inner pressure of said airtight body, said pressure adjusting means communicating with the withdrawing path.

5. A medical apparatus using ozone gas, comprising:
   an ozonizer including means for forming ozone gas, means for feeding ozone gas and means for withdrawing ozone gas;
   a conduit member having a feeding path and a withdrawing path, one end of said conduit member communicating with the gas feeding means and the gas withdrawing means, the feeding path communicating with the gas feeding means and the withdrawing path communicating with the gas withdrawing means;
   a hood having one end connected to the other end of said conduit member and an opposite end which is open; and
   a sprayer of a generally hollow truncated cone shape, said sprayer being provided entirely within said hood, an annular space being formed between said sprayer and said hood, said sprayer communicating with one of the feeding path and the withdrawing path, said annular space communicating with the other of the feeding path and the withdrawing path, said sprayer having an end wall through which is formed a plurality of through-holes through which ozone gas passes, said through-holes and said open end of said hood substantially lying in respective planes, said planes being substantially parallel to each other and spaced only a slight distance from each other.

6. The medical apparatus according to claim 5, wherein said end wall of said sprayer has a concave center section.

7. The medical apparatus according to claim 3, further comprising a skirt made of a soft sheet material, said skirt being fixed around said hood and extending in a direction toward the open end of said hood and ending beyond the open end of said hood.

8. The medical apparatus according to claim 6, in which the sprayer communicates with the feeding path and the annular space communicates with the withdrawing path.

* * * * *